(12) United States Patent
Bring

(10) Patent No.: US 10,632,039 B2
(45) Date of Patent: Apr. 28, 2020

(54) APPARATUS TO FACILITATE THE DELIVERY OF TARGETED PRESSURE THERAPY

(71) Applicant: Benjamin Bring, Columbus, OH (US)

(72) Inventor: Benjamin Bring, Columbus, OH (US)

(73) Assignee: Motiviational Medicine, LLC, Columbus, OH (US)

( * ) Notice: Subject to any disclaimer, the term of this patent is extended or adjusted under 35 U.S.C. 154(b) by 571 days.

(21) Appl. No.: 14/921,909

(22) Filed: Oct. 23, 2015

(65) Prior Publication Data
US 2016/0113834 A1    Apr. 28, 2016

Related U.S. Application Data

(60) Provisional application No. 62/067,649, filed on Oct. 23, 2014.

(51) Int. Cl.
*A61H 7/00* (2006.01)
*A61N 2/00* (2006.01)

(52) U.S. Cl.
CPC .............. *A61H 7/003* (2013.01); *A61H 7/001* (2013.01); *A61H 7/007* (2013.01); *A61N 2/00* (2013.01); *A61H 2201/10* (2013.01); *A61H 2201/1253* (2013.01); *A61H 2201/165* (2013.01); *A61H 2201/1635* (2013.01); *A61H 2201/1645* (2013.01); *A61H 2201/1692* (2013.01); *A61H 2201/1695* (2013.01)

(58) Field of Classification Search
CPC .......... A61H 7/00; A61H 7/001; A61H 7/002; A61H 7/003; A61H 7/007; A61H 2201/1635; A61H 2201/1692; A61H 2201/10; A61H 2201/1695; A61H 2201/165; A61H 2201/1645; A61H 2201/1253; A61N 2/00
See application file for complete search history.

(56) References Cited

U.S. PATENT DOCUMENTS

| | | | |
|---|---|---|---|
| 4,308,860 A * | 1/1982 | Sanders | A46B 1/00 15/227 |
| 4,732,142 A | 3/1988 | Hurlburt et al. | |
| 5,768,709 A | 6/1998 | Newkirk et al. | |
| 6,401,252 B1 | 6/2002 | Dean | |
| 6,669,657 B1 * | 12/2003 | Ongwela | A61H 7/001 601/134 |
| 6,748,604 B2 | 6/2004 | Duboff et al. | |
| 7,707,654 B1 * | 5/2010 | Spence | A61H 7/003 2/161.6 |
| 2003/0236477 A1 * | 12/2003 | Huang | A61H 7/003 601/135 |
| 2004/0064075 A1 * | 4/2004 | Robbins | A61H 7/003 601/107 |
| 2009/0093743 A1 * | 4/2009 | Corzine | A47K 7/028 601/136 |
| 2012/0180192 A1 | 7/2012 | Staszewski | |
| 2014/0088473 A1 | 3/2014 | Mastando | |

* cited by examiner

*Primary Examiner* — Quang D Thanh
(74) *Attorney, Agent, or Firm* — Standley Law Group LLP; Adam Smith; Jeffrey Standley

(57) ABSTRACT

The present invention is an apparatus for reducing the stresses applied to the hands of a therapist and improving the ability of the therapist to accurately apply a desired level of pressure to a patient when performing massage therapy on that patient.

6 Claims, 9 Drawing Sheets

APPARATUS TO FACILITATE THE DELIVERY OF TARGETED PRESSURE THERAPY

CROSS-REFERENCE TO RELATED APPLICATION

This application claims priority to provisional application 62/067,649 filed on Oct. 23, 2014 and is incorporated by reference in its entirety as if fully recited herein.

BACKGROUND AND SUMMARY OF THE INVENTION

Physical therapy and massage therapy are well known and effective methods of treatment of a variety of medical conditions. During therapy sessions, a care provider may apply carefully controlled pressure to precise locations throughout the body using a variety of methods. One such method may use mechanical devices to apply pressure to those locations desired by a care provider. Another method may be the manual application of pressure using the hands of the care provider. Frequently application of pressure by hand is the preferred method of providing treatment due to more consistent feedback between the hand of the care provider and the patient's body. This is in contrast to the use of a mechanical device where the introduction of the device may attenuate the care provider's ability to judge the amount of pressure applied to a patient.

Care providers may frequently be required to care for a large number of patients over the course of a normal workweek. As a care provider may spend an hour or more with each patient, the result may be that the care provider is required to spend several hours every week applying pressure with his or her hands. Unfortunately, such repeated applications of pressure may result in injury to the hand of the care provider including, but not limited to, arthritis, tendinitis, or joint swelling. Such injuries are commonly referred to as repetitive stress injuries and may result in pain and loss of strength in the injured portion of the body. Should a care provider develop such an injury, the result may be the care provider's being unable to provide treatment to his or her patients and, and in some circumstances, becoming patients themselves.

As was noted above, the therapy provided by a care provider may require the application of carefully controlled pressure to specific points on the body of the patient. Others have disclosed various methods of applying splints and pressure devices to the hands of a care provider (see U.S. Pat. Nos. 4,732,142 and 6,669,657). However, these devices do not provide the precision and flexibility necessary to effectively treat patients using deep tissue massage therapy. What is needed is an apparatus for accurately applying hand pressure to a patient that aids in the prevention of repetitive motion injuries to the care provider.

In an embodiment of the invention, a glove may be employed to attach shapes (referred to herein as "massage elements") to various locations on the hand of a care provider where the shapes are designed to provide pressure to the desired body locations. These massage elements may be constructed to provide varying levels of resiliency (for example, providing a soft, firm, or hard interface between the hand of the care provider and the body location to which pressure is to be applied). In certain embodiments of the invention, in addition to varying levels of resiliency and flexibility, these massage elements may vary in size and shape depending upon the intended level of pressure and location to which the pressure is to be applied.

Using massage elements may reduce the stresses applied to a care provider's hand during the provision of treatment to a patient. This reduction in stress may reduce the likelihood and severity of repetitive motion injuries to a care provider. In addition to the reduction of injuries, embodiments of the invention may enable the care provider to provide more effective treatment to a patient. For example, by using a massage element designed to enable a care provider to apply pressure to a specific area, that care provider may be able to deliver a more effective treatment than could be provided through the use of hand pressure alone.

In certain embodiments of the invention, one or more massage elements may be attached to the surface of a glove worn by a care provider. In other embodiments, the massage elements may be contained in pockets or other enclosures located on a glove worn by the care provider. In other embodiments, the massage elements may be attached to an inner surface of a glove worn by a care provider. Embodiments of the invention may employ massage elements that are affixed to the glove in a manner such that they are not ordinarily removable by a treatment provider. In other embodiments, the massage elements may be removable to allow a care provider to attach various massage elements to a glove during the course of a treatment or to facilitate cleaning of the elements or glove.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Massage Elements

Figure 1:
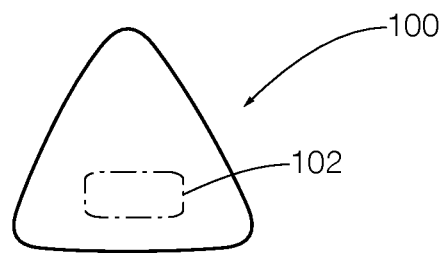
FIG. 1 is an illustration of an embodiment of a massage element according to the invention.

As described herein, massage elements may comprise a variety of shapes, where each shape may be designed to apply pressure to a desired area of a patient's body. For example, an elongated shape 100 as illustrated in by the cross section view of FIG. 1 may be used to apply pressure to a narrow area on a patient. Such a shape may also be useful should a care provider wish to apply a relatively high level of pressure to a desired area of a patient. A wider massage element 200 such as illustrated in FIG. 2 may be used to apply pressure to a larger area of a patient where a narrow shape such as FIG. 1 might result in discomfort. Another embodiment of massage element may be longer with a ridge shape 300 as illustrated in FIG. 3. Such a ridge shape may be useful when applying pressure in a rubbing or rocking motion. Certain embodiments of massage elements may have a pronounced point of contact as illustrated along the ridge of a massage element at 302.

Certain embodiments of the invention may benefit from the use of a semi-rigid material to avoid causing pain or provide a more compliant pressure application point. Other embodiments may require a material able to withstand a higher level of applied pressure without distortion of the massage element. Massage elements may be formed from a rigid or semi-rigid material. Examples of these materials may include, but are not limited to, rubber, plastic, polymer resin, metal, wood, or glass. The use of massage elements may allow a care provider to apply pressure to a patient in a manner that is more focused on the desire area than may be accomplished using a care provider's hands alone. As a result, care provided using massage elements may be more effective than what is provided using a care provider's hands alone.

One skilled in the art will understand that there may be a plurality of shapes used in the formation of massage elements depending on the treatment to be provided to a patient and as a result, massage elements used in embodiments of the invention should not be interpreted as being limited to those shapes illustrated in the figures referenced herein.

Gloves

As described herein, a glove intended to be worn on a care provider's hand may be used to position massage elements at various places on the care provider's hand. By using a glove to position and hold the massage elements in place against a care provider's hand, a care provider may avoid having to grip a massage element with his or her hand, reducing the likelihood of a repetitive stress injury. In addition, through the very use of these massage elements; a care provider may avoid placing excessive stress on his or her hands and fingers. For example, when performing certain medical procedures, a physical therapist may be required to apply pressure to a specific point on a patient's body. Performing such a procedure without an embodiment of the invention may require the physical therapist to apply pressure directly with the tips or his or her fingers. Over the course of providing treatment to a plurality of patients, the physical therapist may become fatigued; losing strength in the fingers of his or her hands and as a result, risk injury to the joints of his or fingers and hands. A device similar to a massage element may be used without being applied to a glove as described herein, however, such devices require that the user grip the device in some manner with their hands, eventually leading to fatigue and the risk of injuries similar to what may occur without using the device. In embodiments of the invention, massage elements may be affixed to gloves worn by care providers. Such embodiments may eliminate the need for a care provider to grip a massage element, allowing the care provider to conserve his or her hand strength for the application of therapeutic pressure to a patient's body. In addition to the full fingered glove illustrated in the figures referenced herein, gloves without one or more fingertips may be used in embodiments of the invention to permit the care provider to make contact directly with the patient when such contact is more beneficial for the treatment type performed by the care provider.

Position of the Massage Elements on a Glove

Figure 4:
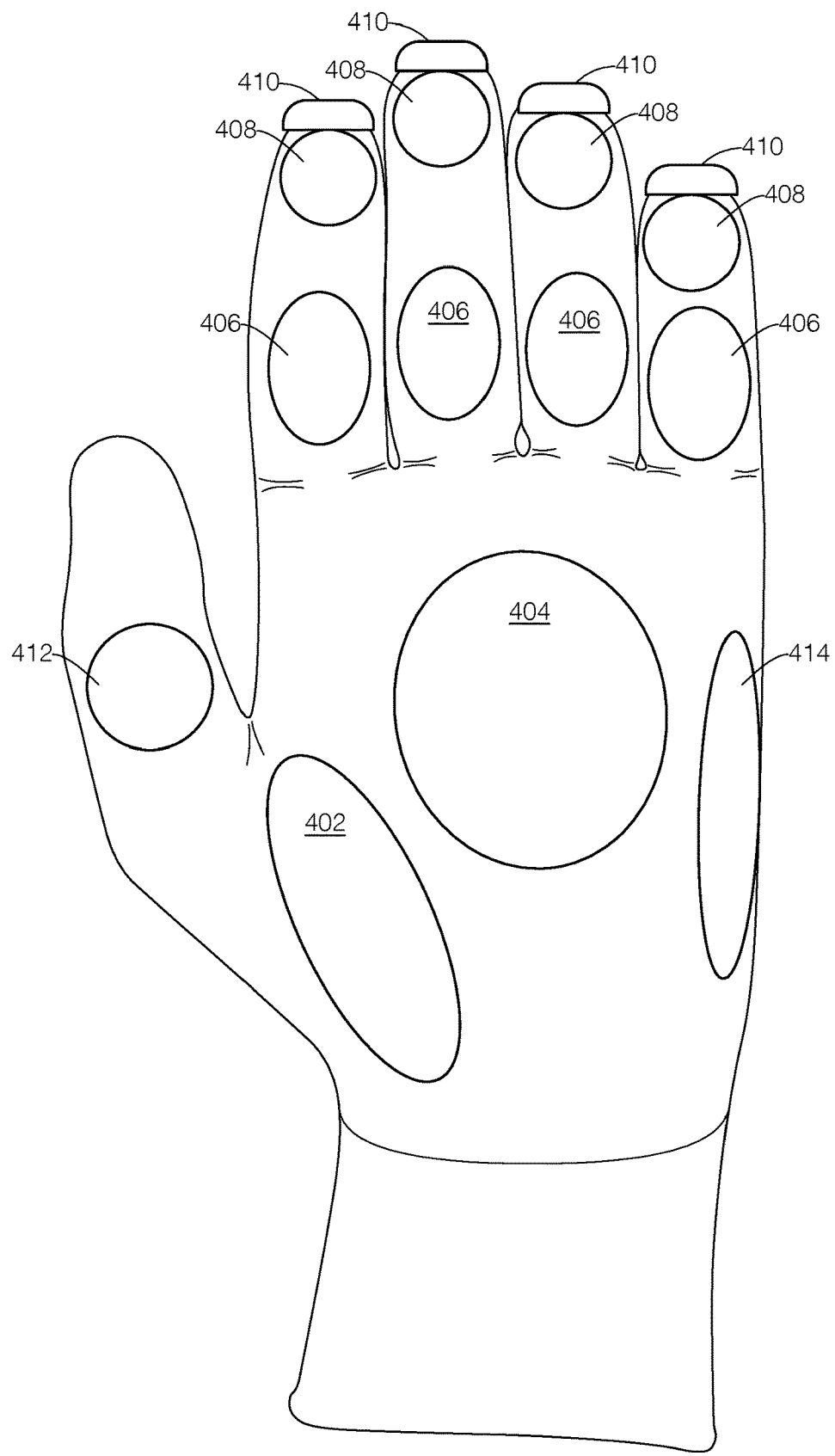
FIG. 4 is an illustration of a glove used in an embodiment of the invention showing the volar surface of the glove used by a care provider to provide therapy to a patient.
Figure 5:
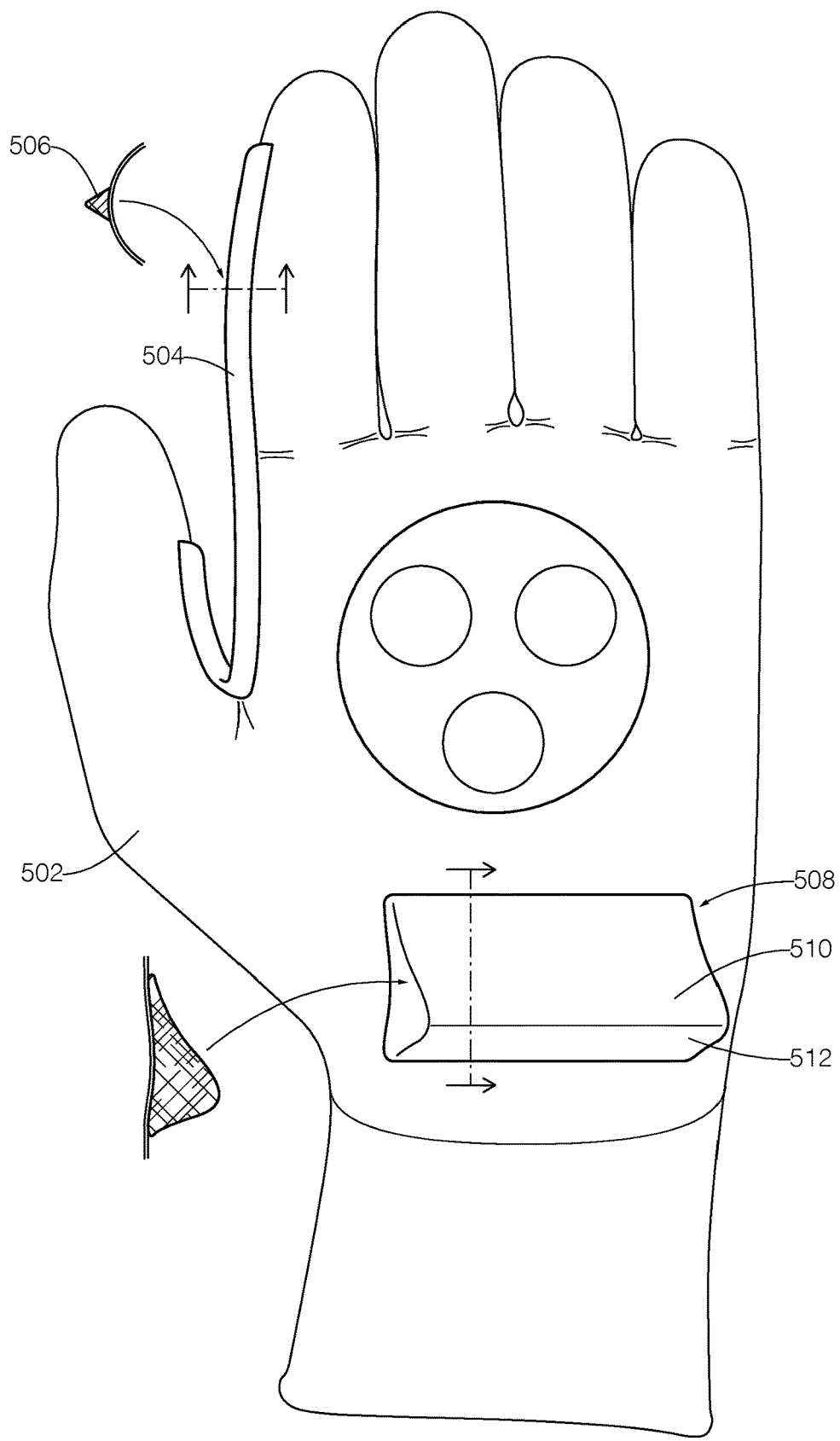
FIG. 5 is an illustration of another embodiment of the invention showing a variety of massage elements attached to volar surfaces of a glove.
Figure 6:
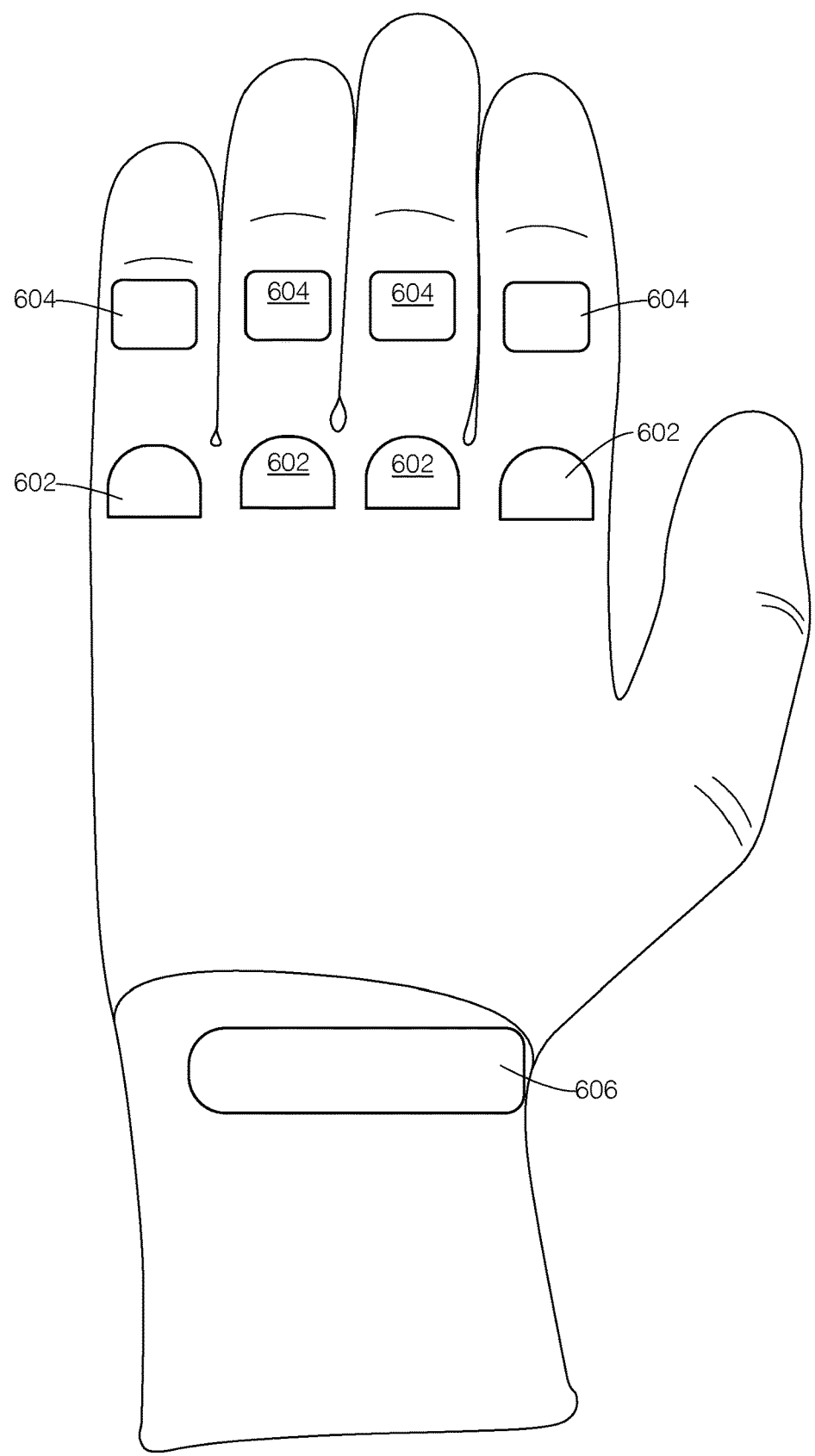
FIG. 6 is an illustration of an embodiment of the invention showing a variety of massage elements attached to the dorsum of the hand.

As illustrated in FIGS. 4, 5 and 6, massage elements may be position at various locations on the volar (palm) surface of a glove. As illustrated in the embodiment of the invention shown in FIG. 4, a massage element may be located on that portion of the glove between the thumb and the wrist, known as the thenar eminence (commonly referred to as the "heel" of the hand) 402, so as to enable a care provider to apply pressure from his or her forearm through their wrist to the heel of the hand where the massage element may be applied to a patient. In another embodiment of the invention, a massage element may be located along the thumb of a glove. This location may allow a care provider to grip a location on the patient to apply therapeutic pressure. FIG. 5 illustrates such an embodiment where the thumb is shown at 502 and the massage element at 504. Referring again to FIG. 4, in other embodiments of the invention, locations may include in the palm of the glove 404, along the fingers at or near the metacarpophalangeal (MCP) joint 406, at the distal interphalangeal (DIP) joint 408, at the distal end of the fingers (finger tips) 410, on the proximal interphalangeal (PIP) joint of the thumb 412, and along the ulnar side of the glove 414. In addition to the volar surface of the glove, in embodiments of the invention, massage elements may be positioned on the dorsal (back) surface of the glove to enable a care provider to utilize portions of the dorsal surface of their hand to apply therapeutic pressure to a patient. An exemplary embodiment of massage elements placed on the dorsal surface is illustrated in FIG. 6. As is shown, massage elements may be located at the dorsal metacarpophalangeal (MCP) joints 602 and at the dorsal proximal interphalangeal (PIP) joints 604.

Specialized Massage Elements

Figure 7A:
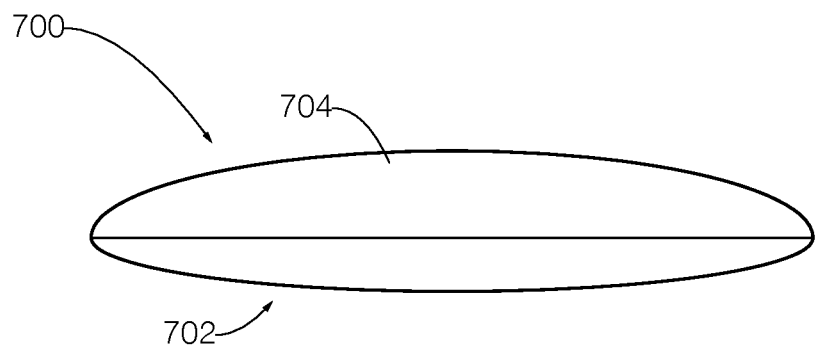
FIGS. 7A, 7B and 7C are illustrations of embodiments of massage elements that are intended to be positioned in the palm area of a care provider's hand.
Figure 7B:
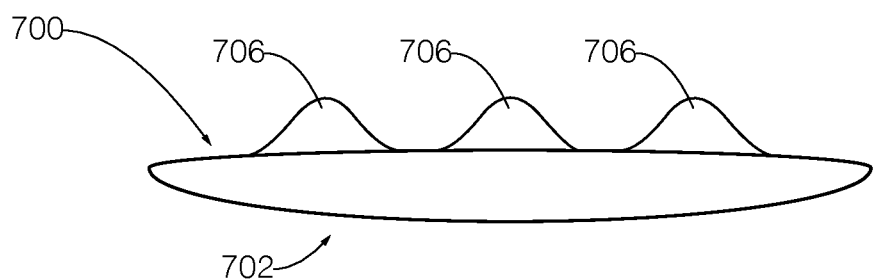

Referring to the cross-section view of FIG. 7A, massage elements 700 located in the palm area may be configured to comprise a broad base 702 which distributes pressure over a wide area of the hand of the care provider. This massage element may also have a correspondingly wide patient contact surface 704 to distribute therapeutic pressure throughout a target area of the patient. In another embodiment of the invention illustrated in FIG. 7B, a massage element located in the palm area may comprise a broad base surface 702, but instead of the upper surface illustrated in FIG. 7A, may have a contact surface comprising a plurality of contact points 706 located on the patient contact surface 708.

Referring again to FIG. 5, a cross section view of the thumb to index finger massage element 504 is shown at 506. The illustrated example is one embodiment of such a massage element. The profile is shown to rise from a broad contact point at the finger to one coming to a narrow profile such that a care provider an apply using the narrow contact point to focus the applied pressure. Also illustrated in FIG.

5 is a massage element 508 that is configured to have a ramp profile 510 that rises from the palm of the care provider's hand to a narrow ridge shape 512. As with the other illustrated massage elements, this ramp profile may permit a care provider to apply force to a patient using the ramp 510 and narrow ridge profile 512 to apply a directed force as the care provider moves his or her hand along an area of the patient requiring treatment. While a limited number of embodiments are illustrated, embodiments of the invention may comprise a greater or lesser number of contact points than illustrated in the figure.

To secure the glove to the hand of the care provider in order to prevent movement of the massage elements relative to the hand of the care provider, various closure methods may be employed. An example of such a method is illustrated as a strap 606 in FIG. 6. Such a strap may employ snaps, buttons, buckles, hook and loop, and other fastener types. Other closure methods may include, but are not limited to, dorsal flaps and elastic materials.

Figure 8:
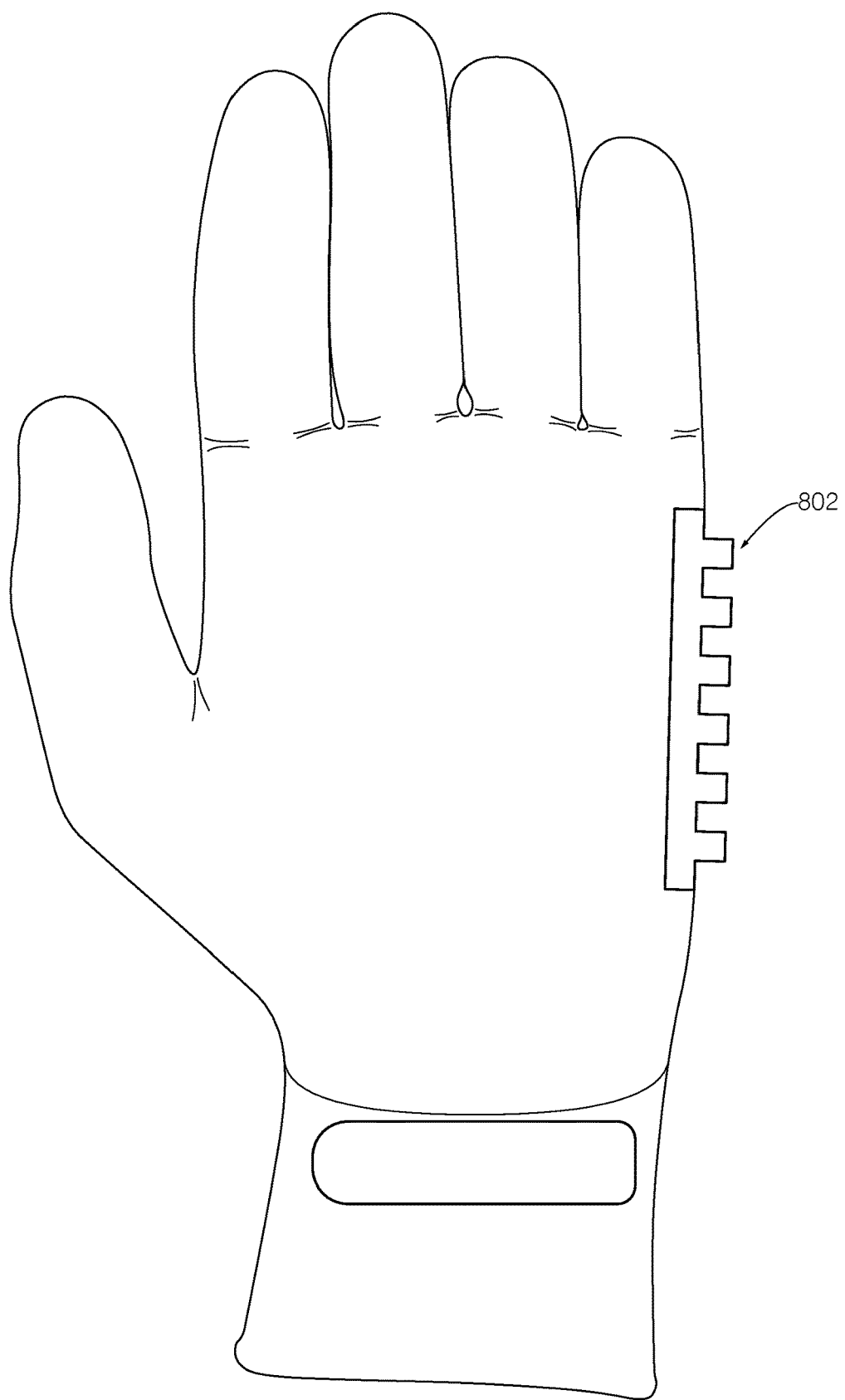
FIG. 8 is an illustration of embodiment of the invention showing a massage element attached to the ulnar portion of the glove, with multiple protrusions extending from the massage element.

In an embodiment of the invention, the ulner side massage element may be configured such that it has a plurality of protrusions as is illustrated in FIG. 8 at 802. These protrusions may be aligned such that they present the appearance of a serrated edge.

Figure 9:
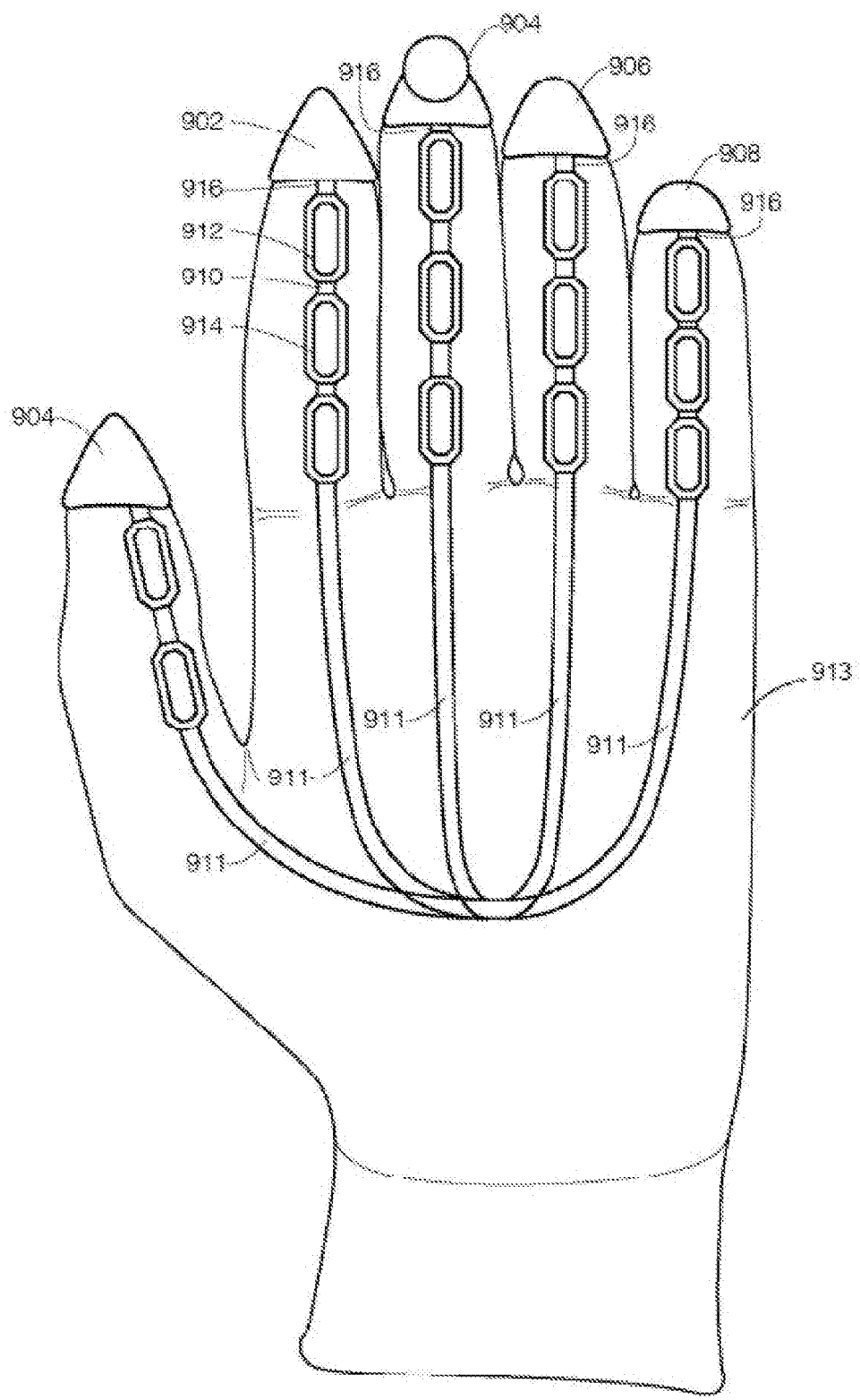
FIG. 9 is an illustration of embodiment of the invention showing massage elements attached to the fingertips of a glove allowing for a pincer grasp.

In certain types of physical therapy and massage therapy provided to a patient, a care provider may wish to apply a pinching pressure to a location on the patient. In an embodiment of the invention, massage elements may be positioned on the ends of a care providers fingers and thumb to facilitate the application of such a pinching pressure. An illustration of such an embodiment is shown in FIG. 9. In the embodiment shown, a first massage element is located at the distal end of a finger 902. A second massage element may be located at the distal end of the thumb 904. As is shown, embodiments of the distal massage elements may be shaped such that they have a more defined point as shown at 902 or may have various other contact surface shapes such as, but not limited to, a spherical contact surface 905, or various curvatures of the contact surface as illustrated the example embodiments shown at 906 and 908. Using these massage elements, a care provider may be able to provide more effective therapy to a patient while reducing the stress applied to the hands of the care provider.

Finger Caps and Straps

In certain embodiments of the invention the massage elements may be connected via an interconnection web. As is illustrated in FIG. 9, the interconnection web 910 may be connected from a first massage element 912 to a second massage element 914. Such a connection may serve to prevent the massage elements from moving relative to one another and the hand of the care provider. This reduction in movement may improve the action of the massage elements by transferring more of the pressure applied by the hand of the care provider to the patient. In certain embodiments of the invention, a distal massage element may be connected to other massage elements using a second interconnection web. This is illustrated at 916 in FIG. 9. As is shown, the massage elements 912 and 914 are fixed in such a way as to allow a user to push against the distal element 902, which in turn pulls the massage elements 912 and 914 using the interaction web 916. Such a configuration will further aid the care provider's provision of pressure to a patient. In certain embodiments of the invention, a third interconnection web 911 may be configured such that it meets interconnection webs from other portions of the glove device. Such an embodiment may provide the care provider additional protection from stress caused by the application of force during treatment. The interconnection web 910, 911, 916 may extend along an outer surface of a flexible glove base 913.

It should be noted that figures disclosed herein should not be interpreted to limit massage elements to only those locations disclosed. Certain treatments may require the application of pressure from various points on a care provider's hand and one skilled in the art will realize that the position of massage elements on a glove may be varied from those depicted herein without departing from the spirit of the invention.

Massage Element Shapes

Figure 2:
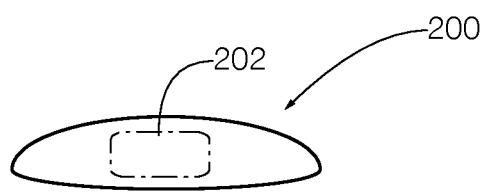
FIG. 2 is an illustration of another embodiment of a massage element according to the invention.
Figure 3:
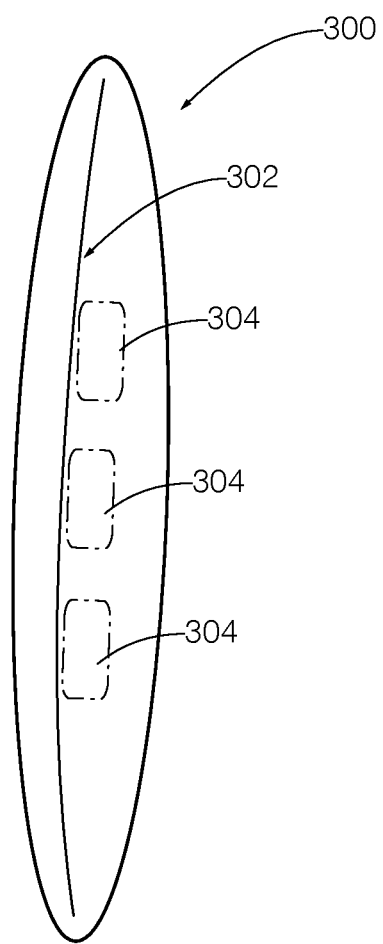
FIG. 3 is an illustration of another embodiment of a massage element according to an embodiment of the invention.
Figure 7C:
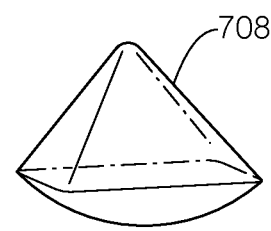
Figure 10:
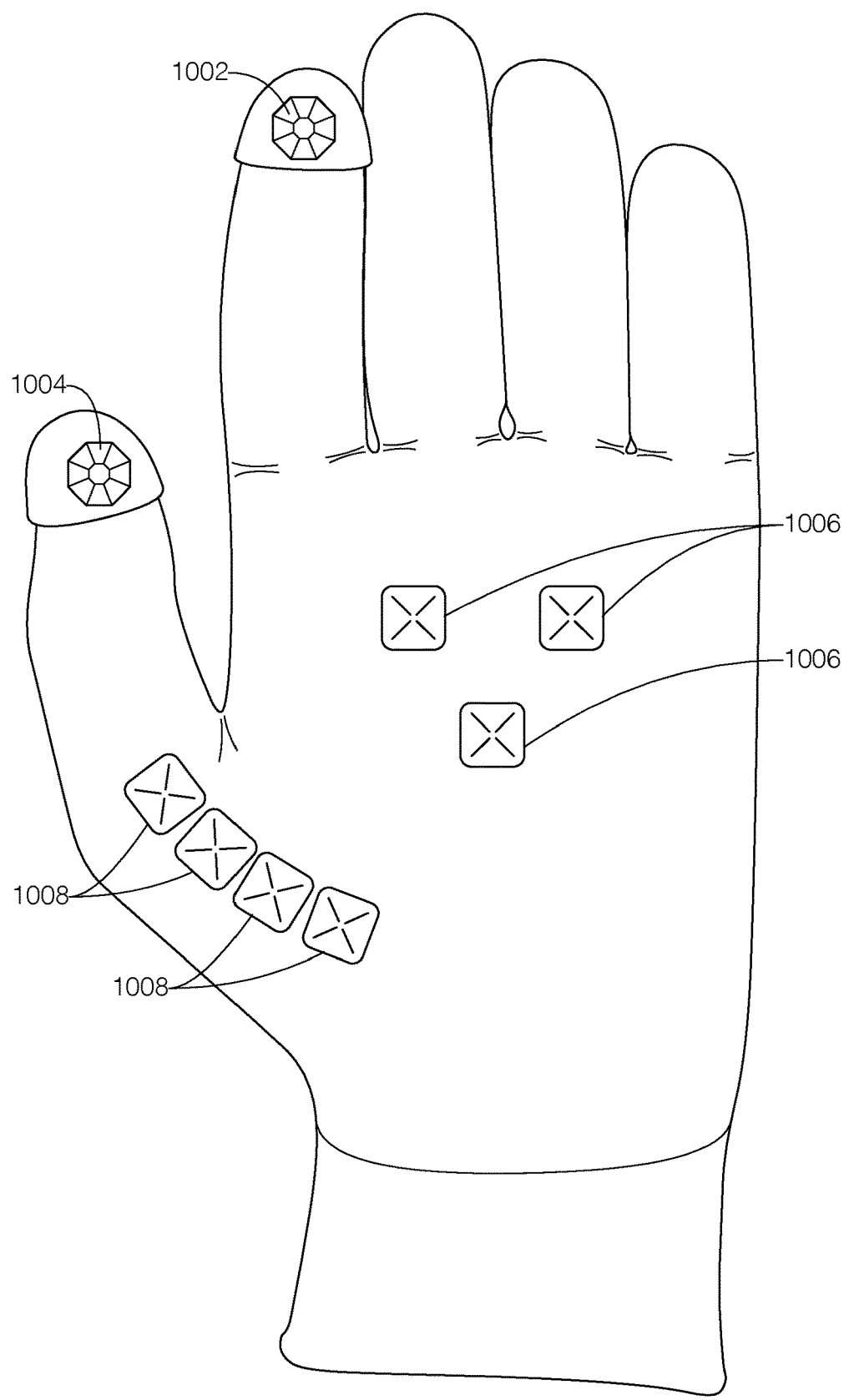
FIG. 10 is an illustration of an embodiment of the invention showing a variety of massage elements attached to volar surfaces of a glove.
Figure 11:
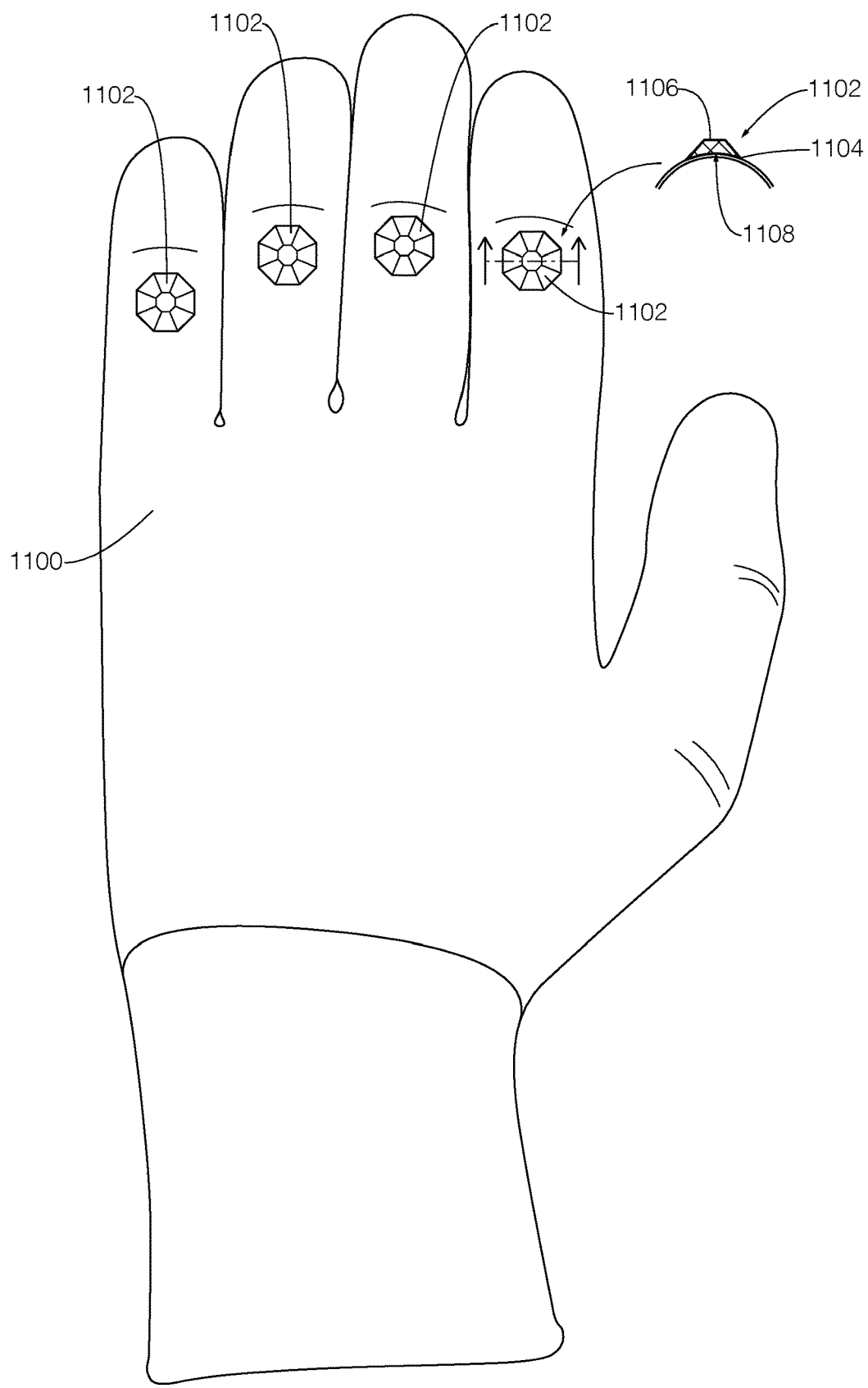
FIG. 11 is an illustration of an embodiment of the invention showing a variety of massage elements attached to the dorsum of the hand.

In addition to the massage elements illustrated in FIGS. 1-3, in certain embodiments of the invention, the massage elements may be pyramid shaped. Such an embodiment is illustrated in FIGS. 7C, 10 and 11. An exemplary pyramid shaped massage element is illustrated in FIG. 11 at 1102. As is shown, the shape extends from a broad base 1104 which may be in contact with the glove and thus the care provider's hand, to a narrower point 1106 which may be applied to a patient in order to provide care. As is illustrated, these pyramid shaped massage elements 1102 may be positioned a various places on the glove 1100 in order to assist the care provider's ability to apply pressure to specific areas of a patient. While, embodiments of the invention should not be limited solely to the disclose locations. Referring to FIG. 10, example embodiments may include the provision of massage elements at the index finger 1002 and thumb 1004 to facilitate the application of pressure via a pinching motion between the thumb and index finger. Such pyramid shaped massage elements may be positioned in the palm area of the glove to permit the care provider to apply pressure with the palm of his or her hand. An example of such an embodiment is illustrated at 1006 and also 708 of FIG. 7C. Another example embodiment of the invention may position the massage elements along the edge of the thumb between the tip of the thumb and the wrist. Such an embodiment is illustrated at 1008 of FIG. 10. As is shown in FIG. 11, massage elements 1102 may be located along the DIP joints of one or more fingers of the glove. As is illustrated, such an embodiment may have a recessed lower surface 1108 in order to interface with the DIP joints of the hand of a care provider using such an embodiment of the invention to provide care to a patient. As is shown, the pyramid shaped massage elements may have a wide base 1104 that narrows to a tip 1106 with a plurality of rounded edges connecting the base to the tip. This structure may allow the care provider to apply pressure to a patient along the tip, the edges, or a combination of both. Such a configuration may be preferred over a more rounded or ball shaped element because the tip and edges may allow the care provider to more easily modulate the pressure applied to a patient.

Magnetic Massage Elements

Research has indicated that as the result of an actual or placebo effect, magnets used in the application of physical therapy may have a positive impact the care delivered to a patient. In certain embodiments of the invention, magnetic inserts may be used to enhance the care provided to a patient. As is shown in FIGS. 1-3, magnets 102, 202 and 304 may be molded or otherwise inserted into massage elements used in embodiments of the invention. One ordinarily skilled in the art will understand that these magnets may vary in size depending upon the size of the massage element into which the magnet is place.

Massage Element Attachment

In certain embodiments of the invention, one or more massage elements may be removably attached to the glove. Such a removable attachment method may serve to allow the elements to be removed for cleaning or replacement. In certain embodiments of the invention, massage elements may be mounted on the surface of the glove. This is illustrated in FIGS. 5 and 9. In other embodiments of the invention, massage elements may be located in enclosures within the glove. In certain embodiments, such enclosures may be configured to allow the massage elements to be removed. In other embodiments of the invention, the massage elements may be located such that they are positioned between the glove and the hand of a care provider when the care provider is wearing the glove to provide treatment to a patient. Such embodiments may permit a massage element to be more firmly in contact with the hand of the care provider, helping to reduce movement of the massage element relative to the care provider's hand.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

What is claimed is:

1. A device to facilitate delivery of targeted pressure therapy comprising:
 a glove comprising:
 a flexible glove base configured to be secured about one or more fingers of a user's hand and cover at least a palm, a finger including a fingertip, and a thumb;
 a first massage element located at and shaped to distribute applied forces over a portion of flexible glove base configured to cover the fingertip;
 a second massage element located at a portion of the flexible glove base configured to cover the finger, wherein the second massage element is spaced apart from the first massage element;
 a third massage element located at a portion of the flexible glove base configured to cover the thumb; and
 a first interconnection web extending along an outer surface of the flexible glove base between and interconnecting the first and second massage elements to a portion of the flexible glove base configured to cover the palm; and
 a second interconnection web extending along the outer surface of the flexible glove base between and interconnecting the third massage element to the portion of the flexible glove base configured to cover the palm;
 wherein the first and second interconnection webs are interconnected with one another at the portion of the flexible glove base configured to cover the palm and are configured to limit relative movement of the first, second, and third massage elements.

2. The device of claim 1, wherein at least one of the first, second, and third massage elements is comprised of a rigid material.

3. The device of claim 1, wherein at least one of the first, second, and third massage elements comprises a base, sides, and a raised portion which faces outwardly from the flexible glove base, wherein said raised portion has a smaller surface area compared to a surface area of said base such that said sides taper between the base and the raised portion.

4. The device of claim 1, wherein at least one of the first, second, and third massage elements has a pyramidal shape.

5. The device of claim 1, wherein at least one of said first, second, and third massage elements comprise a magnet.

6. The device of claim 1, wherein:
 at least one of said first massage element, said second massage element, and said third massage element is configured to be selectively attached to, and selectively removed from, said flexible glove base.

* * * * *